(12) United States Patent
Schall et al.

(10) Patent No.: US 8,968,303 B2
(45) Date of Patent: Mar. 3, 2015

(54) METHOD AND DEVICE FOR TISSUE FUSION OR COAGULATION BY AN ELECTRICAL ACTION WITH NEGATIVE SOURCE IMPEDANCE

(75) Inventors: Heiko Schall, Nuertingen (DE); Achim Brodbeck, Metzingen (DE); Martin Fritz, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 389 days.

(21) Appl. No.: 13/459,286

(22) Filed: Apr. 30, 2012

(65) Prior Publication Data

US 2012/0283733 A1 Nov. 8, 2012

(30) Foreign Application Priority Data

May 3, 2011 (EP) .................................... 11164639

(51) Int. Cl.
*A61B 18/18* (2006.01)
*A61B 18/12* (2006.01)
*A61B 18/00* (2006.01)

(52) U.S. Cl.
CPC ... *A61B 18/1206* (2013.01); *A61B 2018/00827* (2013.01); *A61B 2018/00767* (2013.01)
USPC ........................................... 606/50

(58) Field of Classification Search
USPC ............................................. 606/50
See application file for complete search history.

(56) References Cited

U.S. PATENT DOCUMENTS

| 4,969,885 A * | 11/1990 | Farin ............................. 606/38 |
| 5,720,744 A * | 2/1998 | Eggleston et al. .............. 606/40 |
| 2007/0173803 A1 | 7/2007 | Wham et al. |
| 2009/0234351 A1 | 9/2009 | Desinger et al. |
| 2010/0179534 A1 | 7/2010 | Podhajsky et al. |

FOREIGN PATENT DOCUMENTS

| DE | 102008100383 14 | 1/2010 |
| EP | 1 862 137 A1 | 5/2007 |
| WO | WO 99/65406 | 12/1999 |
| WO | WO 2010/142438 A2 | 12/2010 |

* cited by examiner

*Primary Examiner* — George Manuel
(74) *Attorney, Agent, or Firm* — Dickstein Shapiro LLP

(57) ABSTRACT

In a method suitable for tissue fusion or coagulation, after the start of treatment of the tissue, i.e., after completion of a first phase, a second phase is commenced, during which the biological tissue is treated for a certain specified process time with moderate energy input. The specification of a negative internal resistance of a supplying source enables the process in the second phase to have a treatment time that remains constant and thus avoids premature drying-out of the tissue. A sufficient and reliable bonding of the participating proteins in the moist milieu is reached.

15 Claims, 1 Drawing Sheet

METHOD AND DEVICE FOR TISSUE FUSION OR COAGULATION BY AN ELECTRICAL ACTION WITH NEGATIVE SOURCE IMPEDANCE

RELATED APPLICATION

This application claims priority to European patent application EP 11 164 639.4, filed on May 3, 2011, which is hereby incorporated by reference in its entirety.

TECHNICAL FIELD

Embodiments of the invention relate to a method for tissue fusion or coagulation by at least one electrode that introduces a current into the tissue to be treated.

BACKGROUND

Tissue fusion or coagulation by an electrode that introduces current locally into tissue and/or tissue fluid is known from, for example, EP 1 862 137 A1. In the course of treatment, effects arise in tissue in the vicinity of the electrode that lead to a change in tissue impedance. At the start of the effect, the tissue has an initial impedance that is reduced to a lower value shortly after current starts to flow, designated as "phase I". After a period of time, the tissue impedance rises again, designated as "phase II". The tissue impedance in Phase II generally reaches values that lie markedly above the initial impedance. The rise in impedance then flattens out and may reach a stable end value, referred to as "phase III".

The length in time of phases I and II and the slope of the fall and rise in impedance determine the quality of the surgical result attained.

The system according to EP 1 862 137 A1 therefore attempts to bring the change in tissue impedance over time into line with a target curve. For this purpose, the system continuously compares the actual tissue impedance value measured in a suitable manner to the target value that applies for the particular point in time. If a deviation is found, then a counter-measure is implemented (for example, an increase or decrease in the energy introduced into the tissue). The control technology approach that forms the basis for this technique, however, can reach its limits if control deviations that have led to an irreversible change in tissue structure (e.g., a premature protein denaturation) have occurred.

A robust and reliable method for the performance of tissue fusion or coagulation, in particular long-term sealing of vessels, is therefore desired. A device that enables this method is also similarly sought.

SUMMARY

The method in accordance with embodiments of the invention is based on the introduction of a current into a biological tissue by way of an electrode, as well as the discharge of the current by way of a counter-electrode. A current path through the biological tissue is formed between the two electrodes and represents an electrical tissue resistance. Different phases (i.e., phases I and II, and possibly III) of the time course of tissue resistance result in the introduction of current. The electrical source used to feed the electrode is desirably a controlled high frequency (HF) voltage source. The output voltage of the source corresponds to the process. The electrical current flowing between the electrode and counter-electrode in at least one of the phases, desirably in phase II, is used as the reference variable. The magnitude of the measured current, at least in phase I, is desirably used to regulate the output voltage of the source such that an overall behavior of the source is obtained that corresponds to a source with a desired, negative, internal resistance. The current is desirably measured continuously, or is measured at discrete points in time, for example periodically.

A change to the internal resistance of the source can be simulated through circuit technology using a source with fixed internal resistance, but with variable and controllable voltage. The voltage is set such that, on the basis of the measured current flowing through the tissue, a desired internal resistance of the source is obtained, seen from the electrode and counter-electrode. It is particularly possible to set negative internal resistances; this is desirably carried out during phase II. The value of the (desirably negative) internal resistance is desirably lower than that of the tissue resistance. This ensures a stable mode of operation.

The term tissue resistance can refer to the real component or to the sum of complex tissue impedance.

To control tissue impedance during phase II, a ramp-like increase in voltage, combined with controlling the resistance, can desirably be used as the specification for the source. A functional relationship is desirably defined for this, which is specified by the following equation:

$$u_a = m \cdot t + u_0 - \frac{m \cdot R_G}{AR_0}$$

In this equation, a ramp-like increase in voltage is specified by the parameters m and $u_o$. The last term in this equation represents a resistance term in which the tissue resistance $R_G$ is in a ratio with a reference resistance change $AR_0$ as a time derivative of a reference resistance. This term controls the output voltage such that an increase in the tissue resistance $R_G$ causes a decrease in the voltage $u_a$. During the performance of the method, the change in this tissue resistance over time results from the corresponding setting of the voltage $u_a$ at the electrode. The development of the voltage $u_a$ applied at the electrode and exploiting a negative internal resistance provides the same effect as the control of the tissue impedance with the following relationships. In this case, $u_a = u + R_i * i_a$. $u = m*t + u_o$. $i_1$ is the current flowing through the electrode. The (simulated) internal resistance $R_i$ is desirably negative. The term $-R_i * i_a$ controls the output voltage such that the voltage $u_a$ decreases with an increase in the tissue resistance $R_G$.

If a negative internal resistance and a suitable voltage ramp are used in phase II, then it is possible to keep the time T2 necessary for phase II constant independently of the varying biological conditions in the vicinity of the electrode. In other words, phase II can be carried out in a specified process time. This is conducive to process reliability. It can be ensured that the sequential control to carry out phase II with a timer leads to a desired surgical outcome of consistent quality. In particular, the ramp-like increase in voltage, together with a negative internal resistance of the source during phase II, prevents effects that are the result of premature introduction of too much energy into the tissue, which cannot be reversed by a subsequent reduction in the energy input. The proposed closed-loop or open-loop control strategy is therefore particularly expedient for the regulation of the in-part irreversible and thus largely non-linear processes in phase II.

A device for carrying out the method in accordance with the embodiments of the invention generally comprises at least one unit to provide electrical power, this unit having an electrical source. The device further includes an instrument with at least one electrode that is connected to the unit. The electrode is used to introduce the electrical current into the tissue. A control module captures the current and correspondingly controls the source. Phase II operates with a desirably ramp-like increase in voltage and a desirably negative internal resistance of the source, whereas in phase I, for example, a fixed current, fixed power, fixed voltage and/or fixed and desirably positive internal resistance of the source are used.

Desirably, such a device further contains an instrument recognition mechanism that enables individual parameters, with which the method works in phase II, to be specified. Such parameters are, for example, the increase in voltage m of the ramp, a basic or reference voltage $u_0$ and/or the desired and desirably negative internal resistance $R_i$. For instrument recognition, a code plug or other storage mechanism such as, for example, a storage mechanism provided on the instrument or any other suitable mechanism can be provided that enables at least one of the above parameters to be selected for the instrument. In this way, the same process times T2 can be achieved for different instruments. This enables a high quality of tissue fusion, tissue coagulation, long-lasting vessel sealing and vessel anastomosis to be achieved. The fixed duration of phase II also increases treatment reliability, since the surgeon becomes accustomed to a standard effect time of the instrument on the tissue and adjusts to this.

The above-mentioned instruments can be monopolar instruments, or desirably bipolar ones, such as vessel clamps, the two clamping limbs of which can be formed as the electrode and counter-electrode. Such vessel clamps are used for long-term vessel sealing. Such a device clamps a vessel and seals it through the adherence to one another of opposing tissue walls pressed against each other. Moreover, such an instrument can contain a knife to cut through the sealed vessel.

Monopolar instruments used within the scope of the embodiments of the invention can have electrodes with e.g., a plate or spherical shape, a loop shape or other shape. The counter-electrode does not participate in the surgical effect. It is attached, for example as a neutral electrode, to the patient.

BRIEF DESCRIPTION OF THE DRAWINGS

Hereinafter, exemplary embodiments of the invention are explained in greater detail with reference to drawings, in which.

DETAILED DESCRIPTION

Figure 1:
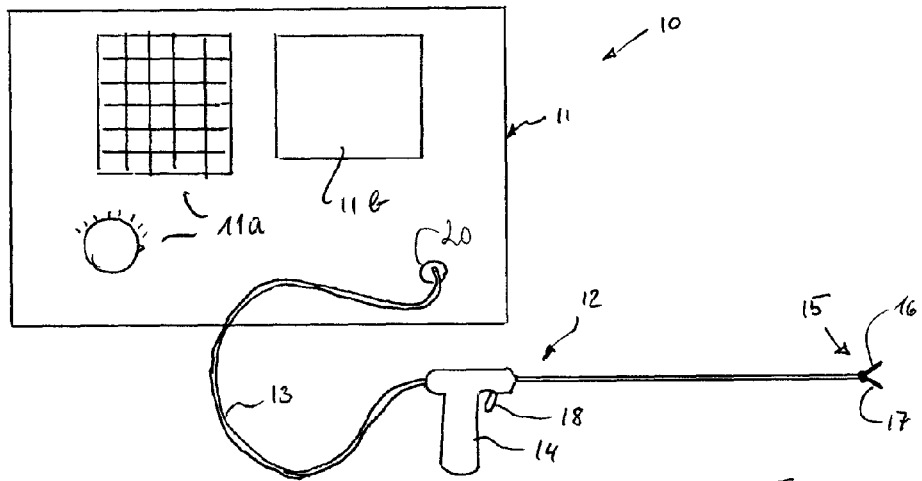
FIG. 1 shows a schematic representation of a device for vessel sealing.

FIG. 1 shows a device 10 that represents an example of different devices suitable for tissue coagulation. The device 10 comprises a unit 11 for supplying and operating a surgical instrument 12. The unit 11 has one or more operating elements 11a and at least one display element 11b in the form of a display device. The instrument 12 is connected via a line 13 to the unit 11. The instrument 12 is provided with voltage from the unit 11 via the line 13.

The instrument 12 in the present embodiment is a bipolar vessel clamp with a handle 14 and a tool 15. The latter comprises an electrode 16 and a counter-electrode 17, of which at least one, in this embodiment both, is mounted such that they can be moved. The electrode 16 and a counter-electrode 17 can be moved towards and away from one another by the actuation of a hand lever 18. The instrument 12 does not necessarily have to be a bipolar instrument, as shown here. Monopolar instruments that have just one electrode can also be used. The counter-electrode is then, for example, a neutral electrode to be secured to the patient over as large an area as possible.

Figure 2:
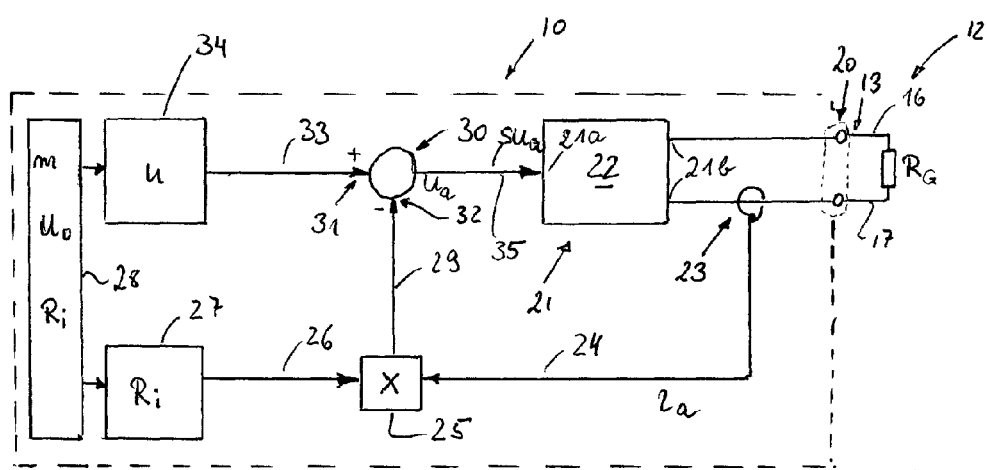
FIG. 2 shows a block diagram of the device according to FIG. 1.
Figure 4:
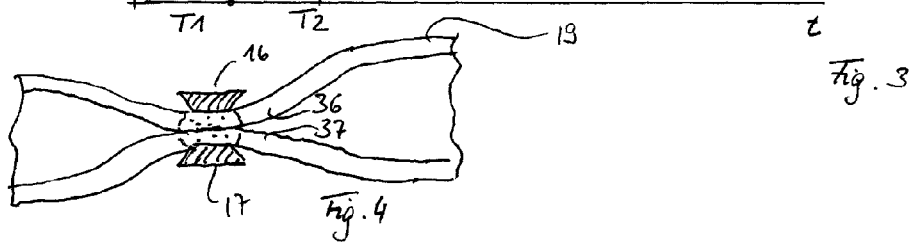
FIG. 4 is a schematic sectional representation of a longitudinal cut of a vessel during vessel sealing.

The basic electrical structure of the device 10 is shown in FIG. 2. A resistance $R_G$ symbolizes the impedance, which in the simplest case is the ohmic resistance of the tissue 19 gripped between the electrodes 16, 17. Such tissue 19 can, for example, be a blood vessel, as shown in FIG. 4.

The electrodes 16, 17 are shown in FIG. 2 solely as lines reduced to their electrical function. They are connected to the unit 11 via the line 13 and a plug connector 20.

The instrument 12 is supplied with electrical power by a source 21, which is a DC or AC voltage source, desirably a high frequency (HF) generator 22. The source 21 provides, at output 21b, a high-frequency AC voltage, for example in the range of several hundred kilohertz and if necessary several hundred volts, and also over a thousand volts for cutting, contact-free coagulation or ablating applications. The amplitude of the HF voltage $u_a$ corresponds to a voltage signal $su_a$ received at control input 21a. The HF generator 22 delivers the HF power to the electrode 16 and the counter-electrode 17. A current sensor 23 may be arranged in one of the corresponding lines, for example in the line leading to the counter-electrode, and generates a signal that characterizes the current flowing through the tissue. The signal or the effective value desirably characterizes the sum of the current and is itself therefore not a high frequency signal. The signal can be supplied via a desirably electronic rectifier, which desirably delivers a smoothed signal. The smoothing can be carried out with an RC element. The time constant is desirably less than one second so that rapid rises or falls in current can be adequately shown in the signal.

The signal characterizing the current is fed via a signal path 24 as an input signal to a multiplier 25. The multiplier 25 receives, via a further signal path 26, a further input signal $R_i$, which is made available by a block 27. The signal $R_i$ characterizes an internal resistance that is effective as a generator internal resistance between the electrode 16 and the counter-electrode 17. The signal $R_i$ may have positive or negative values. Its magnitude and its sign are determined by a system controller 28 that controls the block 27 accordingly.

The multiplier 25 multiplies the signals received via the signal paths 24, 26 and delivers the product via a further signal path 29 to a summer 30. The summer 30 has a non-inverting input 31 and an inverting input 32 and hence forms the sum with a sign i.e., the difference between the signals it receives at the two inputs 31, 32. The summer 30 may be formed by a differential amplifier.

While the signal path 29 is connected to the inverting input 32, the non-inverting input 31 receives a voltage signal u from a block 34 via a signal path 33. The voltage signal u can have a pre-determined time course, which is formed by the block 34. The signal u desirably follows a time course corresponding to:

$$u = m^* t + u_0.$$

This is a linear equation. The rise m and the constant term $u_0$ are specified according to the purpose by the system controller 28.

A signal path 35 leads from the summer 30 to the control input 21a of the HF generator 22. The control signal $u_a$ present there satisfies the relationship:

$$u_a = u - R_i * i_a$$

where $i_a$ is a signal that characterizes the current flowing through the tissue and captured by the current sensor 23.

The multiplier 25, summer 30, blocks 27, 34, system controller 28 and the rectifier/effective value-former of the current signal can be realized by specific circuits or by software. In particular, they can be programs or sections of programs of one or more microcontrollers.

Figure 3:
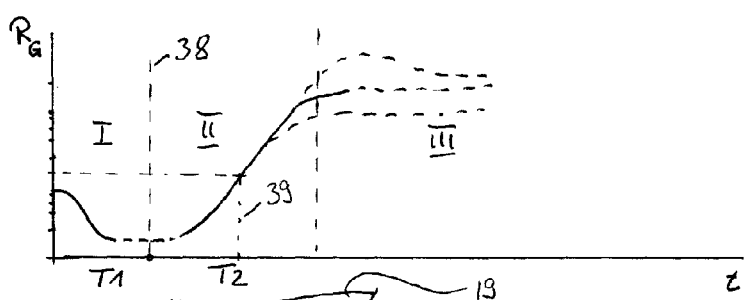
FIG. 3 shows a diagram to illustrate the course of tissue resistance over time.

The device 10 works as follows:

It is assumed that a user of the instrument 12 wishes to seal a blood vessel 19 (FIG. 4). The user therefore grips the blood vessel 19 between the electrode 16 and the counter-electrode 17 and actuates the hand lever 18 to press opposing sections 36, 37 of the wall of the blood vessel 19 against one another. A suitable measure e.g., the actuation of the hand lever 18, actuation of another switch arranged on the hand grip 14 or on a foot switch, then activates the delivery of power by the unit 11. As long as no current flows to the blood vessel 19, it has an initial impedance of, for example, 50 ohms or a similar value. This is shown in FIG. 3 in the time interval T1. The tissue resistance $R_G$ is shown logarithmically on the vertical scale.

Once current is flowing through the tissue, the tissue resistance $R_G$ falls relatively rapidly. Individual cells open, for example, and current paths filled with electrolytes are formed. In this first phase I, it is possible to work according to a suitable fixed mode for example, a constant voltage $u_o$, with constant power, with constant current or according to other criteria. This may be set in advance. It is also possible for the unit 11 to be configured such that the individual modes for phase I can be selected or adjusted. It is also possible for an instrument recognition mechanism to be provided that, for example, works together with a storage mechanism provided in the instrument 12, and which correspondingly sets the operating mode of the HF generator 22/source 21.

The progress of the process is monitored during phase I so that the start of phase II can be recognized. Monitoring can, for example, be carried out by monitoring the flowing current or by monitoring other physical variables such as the phase angle of an electrical variable, the current, the voltage between the electrode 16 and the counter-electrode 17 or the tissue resistance $R_G$. The time curve in FIG. 3 shows that it is possible to use the first renewed rise in tissue resistance $R_G$ (after it has reached a minimum) as a sign of the start of phase II. This is indicated in FIG. 3 by a vertical dashed line 38. It is, however, also possible to set other limit values or threshold values. For example, the start of phase II can also be defined as that point in time at which a tissue resistance $R_G$ that lies markedly above the tissue resistance measured at the start of phase I is reached again for the first time. This is indicated in FIG. 3 by a second vertical dashed line 39.

Regardless of how the starting point of phase II is defined, at the start of phase II, the unit 11 switches to a phase II operating mode that differs from the previous operating mode. In phase II, the unit 11 simulates a negative internal resistance $R_i$ of the source 21 (the HF generator 22 in this embodiment). This has a low positive internal resistance or an internal resistance of virtually zero. However, the output voltage $u_a$ follows the measured current $i_a$ such that, from the perspective of the tissue resistance $R_G$, the supplying source 21 has a negative internal resistance $R_i$. The value of the negative internal resistance $R_i$ is desirably lower than that of the tissue resistance $R_G$.

The signal characterizing the current $i_a$ is multiplied in the unit 11 by the desirably negative internal resistance $R_i$, and the resultant signal is supplied via the signal path 29 to the summer 30. The difference between a voltage u and the product of $i_1$ and $R_i$ is formed here. The voltage u follows a time ramp with the initial value $u_0$ and the increase m. The variables $R_i$, m and $u_0$ are desirably specified specifically for the instrument using an instrument recognition mechanism. Desirably, they cannot be changed or at least not readily changed by the user.

The use of a negative internal resistance $R_i$ means that a falling current $i_a$ flowing through the tissue leads to a decreasing generator voltage and vice versa. An increasing tissue resistance $R_G$ leads to a decreasing voltage $u_a$. As a result of the additional effect of the ramp function, the more rapidly the tissue resistance $R_G$ increases, the more slowly the voltage $u_a$ rises, and the entry of energy into the tissue. This leads, in phase II, to a specified process time T2 (FIG. 3). The process time T2 can be kept largely constant for larger or smaller vessels and independently of physiological differences between individual patients, thus leading to a high treatment reliability and dependably high quality of tissue fusion.

The end of phase II is reached once the specified process time T2 has elapsed. The coagulation process can then be continued in phase III or stopped depending on suitable requirements.

In the method suitable for tissue fusion or coagulation after the start of the treatment of the tissue, i.e., after phase I is over, phase II is commenced during which the biological tissue is treated with moderate energy input for a certain fixed process time. By the specification of a negative internal resistance of a supplying source 21, it is possible for the process in phase II to take the same length of treatment time, hence avoiding premature drying-out of the tissue. A sufficient and reliable bonding of the participating proteins in a moist milieu is achieved.

What is claimed is:

1. A method of tissue fusion or coagulation using at least one electrode and a counter-electrode connected to an electrical source, said method comprising:
    determining a current flowing between the electrode and counter-electrode using a tissue resistance; and
    controlling a voltage delivered by the electrical source using the current captured between the electrode and the counter-electrode, the electrical source having an internal resistance that is at least temporarily negative.

2. The method according to claim 1, wherein a functional relationship is specified for controlling the voltage as a function of the current.

3. The method according to claim 2, wherein the internal resistance of the electrical source is simulated with the functional relationship.

4. The method according to claim 2, wherein parameters used in the controlling step include a voltage increase, a constant term and/or a phase duration and/or the internal resistance.

5. The method according to claim 4, wherein for at least one of the parameters, a plurality of values are stored in a storage device, of which one value is selected depending on a type, size or design of a connected instrument.

6. The method according to claim 1, wherein the internal resistance has a value greater than or equal to zero during a phase in which tissue impedance initially has a tendency to fall before remaining at approximately the same level.

7. The method according to claim 1, wherein during the controlling step, a functional relationship, given by $$u_a = m \cdot t + u_0 - \frac{m \cdot R_G}{AR_0}$$

is used, where m represents an increase in voltage, t is time, $u_0$ is a voltage constant, $AR_0$ is a reference resistance change and $R_G$ is a tissue resistance.

8. The method according to claim 1, wherein the internal resistance is fixed at a negative value during a phase in which tissue impedance has an increasing tendency.

9. The method according to claim 1, wherein the controlling step is divided into at least two phases, a first phase characterized by a reduction in tissue resistance and a second phase characterized by a rise in tissue resistance, wherein at least the second phase has a specified constant duration.

10. The method according to claim 9, wherein a transition from the first phase to the second phase is determined using the tissue resistance passing through a minimum resistance.

11. The method according to claim 1, wherein the electrical source delivers a high-frequency AC voltage.

12. A device for tissue fusion or coagulation using a high-frequency alternating current, said device comprising:
an electrical source having an output for delivering a high-frequency AC voltage with an internal resistance that is negative at least temporarily,
at least one electrode connected to the output and configured to be brought into interaction with a biological tissue to bring about a surgical effect, and
at least one counter-electrode connected to the output and configured to be brought into electrical connection with the biological tissue.

13. The device according to claim 12, further comprising:
a current sensor for an ongoing determination of an electrical current flowing between the electrode and counter-electrode, the current sensor for generating a signal characterizing the electrical current, and
a control module connected to a control input of the source and which makes a control signal available on a basis of the signal supplied by the current sensor, which is applied to the control input of the source and which determines the magnitude of the voltage delivered by the electrical source,
wherein the control module specifies a negative internal resistance of the electrical source in at least one of several operating phases.

14. The device according to claim 12, wherein the internal resistance during a first phase, in which the tissue impedance initially has a falling tendency and then has an approximately constant tendency, is specified as a positive value.

15. The device according to claim 14, wherein the internal resistance during a second phase, in which the tissue impedance has a rising tendency or initially a constant tendency and then a rising tendency, is specified as a negative value.

* * * * *